(12) United States Patent
Vallittu

(10) Patent No.: US 8,864,825 B2
(45) Date of Patent: Oct. 21, 2014

(54) IMPLANT SYSTEM

(75) Inventor: Pekka Vallittu, Kuusisto (FI)

(73) Assignee: Skulle Implants Oy, Turku (FI)

( * ) Notice: Subject to any disclaimer, the term of this patent is extended or adjusted under 35 U.S.C. 154(b) by 225 days.

(21) Appl. No.: 13/516,767

(22) PCT Filed: Dec. 10, 2010

(86) PCT No.: PCT/FI2010/051009
§ 371 (c)(1),
(2), (4) Date: Jul. 19, 2012

(87) PCT Pub. No.: WO2011/073507
PCT Pub. Date: Jun. 23, 2011

(65) Prior Publication Data
US 2012/0277743 A1 Nov. 1, 2012

(30) Foreign Application Priority Data
Dec. 18, 2009 (FI) .................................... 20096351

(51) Int. Cl.
*A61F 2/02* (2006.01)
*A61L 27/50* (2006.01)
*A61L 31/14* (2006.01)
(52) U.S. Cl.
CPC *A61L 27/50* (2013.01); *A61L 31/14* (2013.01)
USPC .................................... 623/11.11; 623/23.76

(58) Field of Classification Search
CPC ................................ A61F 2/28; A61F 2/3094
USPC ..................... 623/11.11, 16.11, 18.11, 23.76; 428/221–301.4
See application file for complete search history.

(56) References Cited

U.S. PATENT DOCUMENTS

| 6,197,410 | B1 | 3/2001 | Vallittu et al. ............. 428/292.1 |
| 2002/0022885 | A1 * | 2/2002 | Ochi .......................... 623/16.11 |
| 2008/0154373 | A1 | 6/2008 | Protopsaltis et al. ...... 623/17.12 |
| 2010/0076556 | A1 * | 3/2010 | Tomantschger et al. ... 623/11.11 |

FOREIGN PATENT DOCUMENTS

WO        WO 99/45890        9/1999

* cited by examiner

*Primary Examiner* — Jason-Dennis Stewart
(74) *Attorney, Agent, or Firm* — James C. Lydon

(57) ABSTRACT

The present invention relates to an implant system comprising implantable material in at least partially uncured form, contained in a closed casing, under vacuum and sterilized, and a closed bag containing the casing. The system is characterized in that at least 5% of the surface of the casing comprises sheet-like material having a thickness of 0.05-5 mm and having an original form, the sheet-like material being selected from the group consisting of metallic materials, polymers, bioceramic materials and composites thereof, provided that the material, once deformed from its original form to a changed form, is capable of maintaining that changed form unless subjected to external forces.

18 Claims, 4 Drawing Sheets

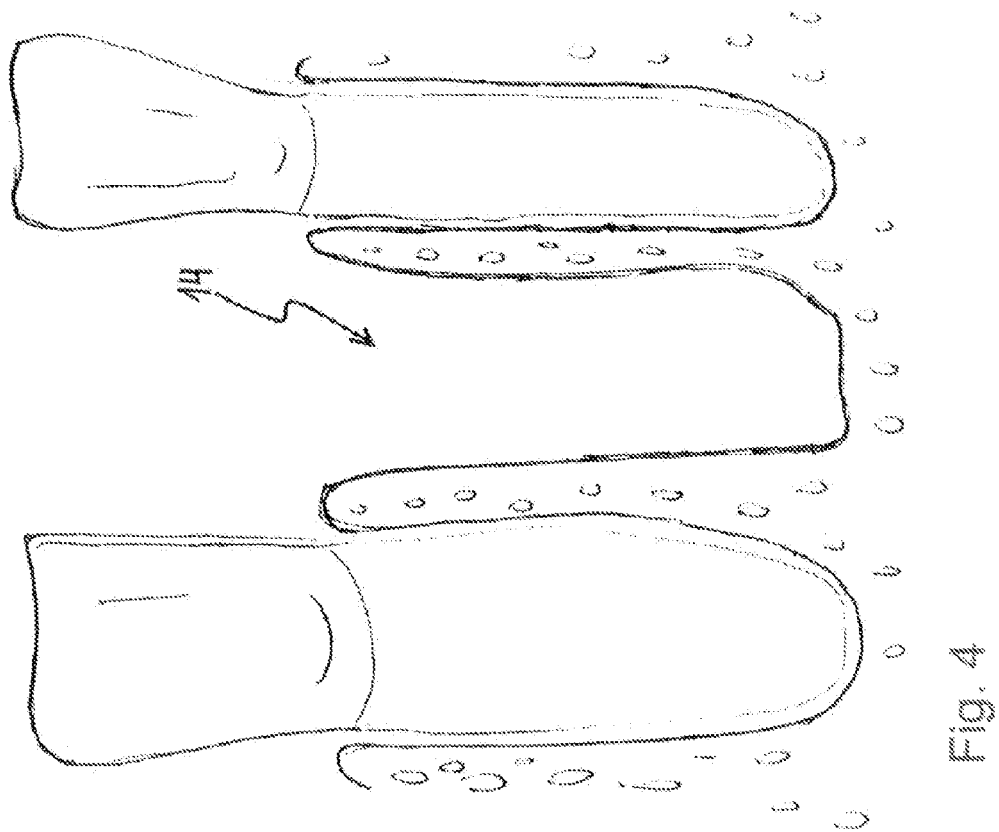
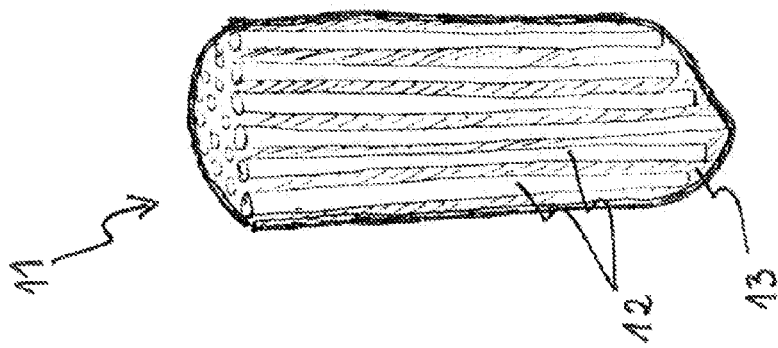
Fig. 4

IMPLANT SYSTEM

FIELD OF THE INVENTION

The present invention relates to an implant system comprising implantable material in at least partially uncured form and contained in a closed casing under vacuum and sterilised as well as a closed bag containing the casing. The invention also relates to an implant obtainable from said implant system as well as to a method for manufacturing an implant.

BACKGROUND OF THE INVENTION

Various implant materials are known in the art and are widely used. Some promising implant materials, especially for bone implant for correcting defects in bones, are different composites comprising bioactive glass and hydroxyapatite. Typically, these materials are mouldable and soft before they are cured to form a solid piece used as an implant. Typical problems in this field are the shaping of the implant material, as this is usually made by hands by the surgeon, which includes a risk of contamination of the implant material.

Document WO 2008/079861 discloses an implant having a bio-compatible sheath and a curable material sealed within the sheath. The curable material is cured once the implant is positioned in its final position. The primary functions of the sheath are to contain the curable material and to influence or control the shape of the implant, prior to the completion of the curing. The document also discloses a package containing the implant precursor, whereby the package is opened only once the implant is ready to be positioned, thus obtaining a sterile implant precursor. The sheath is, however, not removed, but forms an integral part of the finished implant.

Document EP 398 497 discloses a method for moulding implants, where an implant precursor is arranged in a flexible bag, the bag is positioned to the final position of the implant, the precursor is rigidified by vacuum and cured. The bag may be removed after curing and it can be made, for example, from fluorocarbon polymer or latex and it is an open enclosure.

OBJECTS AND SUMMARY OF THE INVENTION

An object of the present invention is to provide an implant system where it would be safe to correctly shape the implant material to the required, sometimes quite complicated shape and then to be able to cure the implant material to this exact shape.

Another object of the invention is to provide an implant system where the risks of contamination of the patient can be minimised, i.a. by avoiding contact between the surgeon and the implant material and between the possibly irritating components of the uncured implant material and the patient.

A yet further object of the invention is to provide an implant system where the finished implant has improved adhesion to the surrounding tissues.

The above-mentioned objects are achieved at least partially by the present invention, which relates to an implant system that comprises implantable material in at least partially uncured form, contained in a closed casing, under vacuum and sterilised, a closed bag containing the casing and wherein at least 5% of the surface of the casing comprises sheet-like material having a thickness of 0.05-5 mm, the sheet-like material being selected from the group consisting of metallic materials, polymers, bioceramic materials and composites thereof, provided that the material, once deformed, is capable of maintaining that form unless subjected to external forces.

BRIEF DESCRIPTION OF THE DRAWINGS

FIG. 4 shows a use of an implant system according to a second embodiment of the invention.

DETAILED DESCRIPTION OF THE INVENTION

Figure 1:
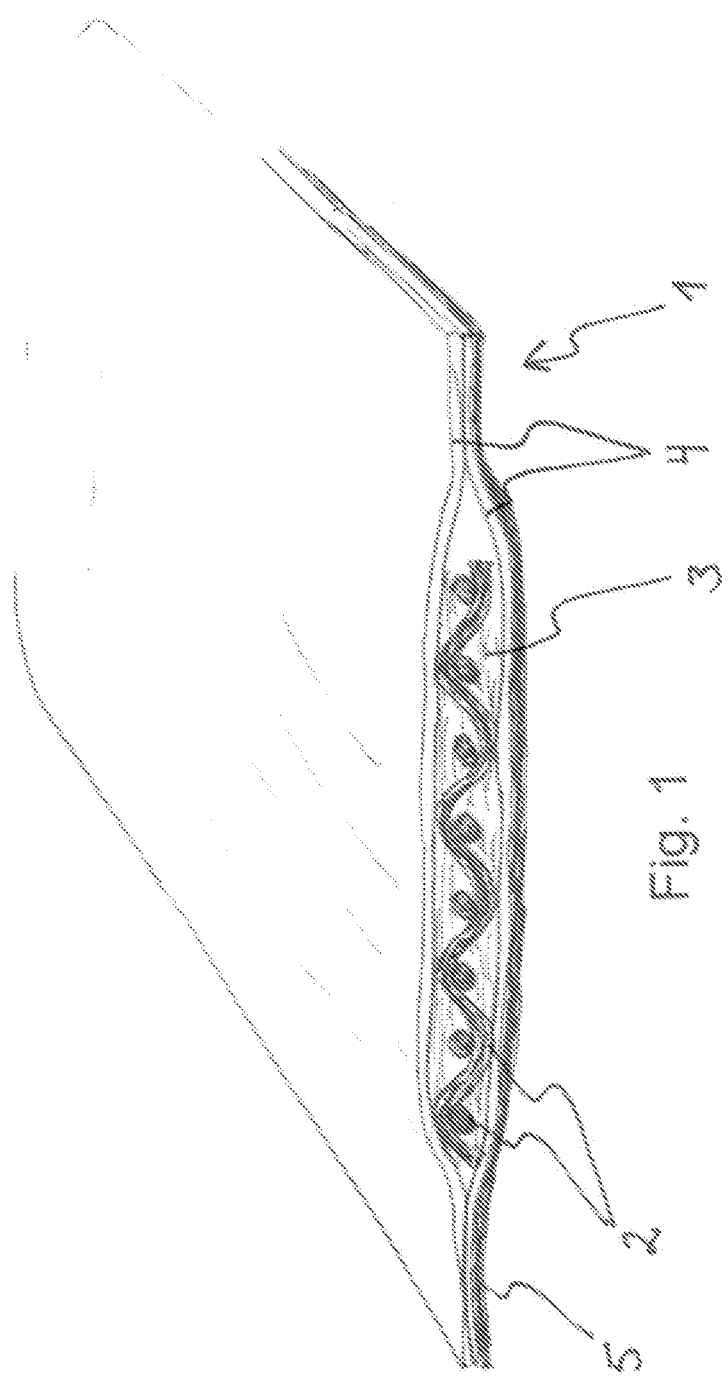
FIG. 1 shows a cross-sectional view of an implant system according to a first embodiment of the invention.

A typical example of an implant system according to the present invention comprises
  implantable material in at least partially uncured form, contained in a closed casing, under vacuum and sterilised,
  a closed bag containing the casing,
wherein at least 5% of the surface of the casing comprises sheet-like material having a thickness of 0.05-5 mm and having an original form, the sheet-like material being selected from the group consisting of metallic materials, polymers, bioceramic materials and composites thereof, provided that the material, once deformed from its original form to a changed form, is capable of maintaining that changed form unless subjected to external forces.

The materials are thus selected such that once deformed, they maintain that form unless they are subjected to further deformation by external forces. By maintaining a form it is meant that the possible deformation is less than 5% during 60 minutes. Typical materials capable of this are metals but also some polymers and bioceramic materials as well as composites of at least two thereof. By external forces it is meant forces exceeding the force of gravity.

The deformation is measured as bending at a speed of 5 mm/min, according to the standard ISO 10477:92.

The present invention thus provides an implant system where the implantable material can be shaped while it is still protected by a closed casing and it is sterile. This thus avoids any risk of contamination by a contact between the surgeon and the implant material and between the possibly irritating components of the uncured implant material, such as monomers, and the patient. Furthermore, the active surface of the finished implant improves its adhesion to the surrounding tissues, which may be for example bone or soft tissue.

By closed casing or closed bag it is meant a casing or bag that is sealed or otherwise closed in such a manner that its contents are not in contact with the outside atmosphere. The vacuum applied to the closed casing is typically only a small underpressure, such as 0.01 to 0.1 bars, for example 0.04 bars (ca. 14.7 psi). Indeed, when the implantable material is in the form of a prepreg comprising resin matrix, the vacuum package eliminates air bubbles from the resin, allows a better monomer conversion of the resin during polymerization because oxygen inhibition of the free radical polymerization does not take place under vacuum package. As an example, it can be said that the permeability of a vacuum package film of copolymer PVC/PVdC (polyvinylchloride/polyvinyldichloride) film at −1° C. is 2.0 and 0.6 mL m$^{-2}$ 24 h$^{-1}$ atm$^{-1}$. Lowering the temperature from 23° C. to −1° C., the oxygen permeability is lowered by one fiftieth, and at the same time the storage time of the material is increased due to hindered spontaneous autopolymerization of the monomers of the resin matrix of the composite prepreg.

Implantable material in this context means the material that will form the implant once it is cured, such as polymerised. The implantable material is thus still in a shapable form and here at least partially in uncured form. The implantable material may also be called the composite material or the prepreg. Curing of the implantable material is preferably induced by light, but naturally also other curing methods can be used, such as heat, ultraviolet irradiation and microwave irradiation.

In this description, by sheet-like material it is meant material, the thickness of which is considerably smaller than its other two dimensions. The other two dimensions, i.e. the width and the height are typically in the same order of magnitude. The sheet-like material can be plate, foil, flat wire or mesh. The sheet-like material is such that it can be bent by hand to the desired anatomical form and it retains its shape by providing support to the implant material such that it retains that shape until polymerisation. The force provided by the sheet-like material should exceed the force of the shape memory effect of the implant material in its non-cured or partially cured form.

The thickness of the sheet-like material is from 0.05 to 5 mm, typically 0.1-0.5 mm. The thickness also depends on the material selected, and could be, for example, around 0.2 mm for a metal foil. The thickness can be, for example, from 0.05, 0.09, 0.1, 0.15, 0.2, 0.23, 0.3, 0.4, 0.5, 0.9, 1, 1.5, 2.3, 2.5, 3 or 4 mm up to 0.1, 0.15, 0.2, 0.3, 0.4, 0.5, 0.9, 1, 1.5, 2.3, 2.5, 3, 3.5, 4, 4.5 or 5 mm.

The sheet-like material is selected from the group consisting of metallic materials and bioceramic materials. The metallic material can be, for example, aluminium, tin, iron, steel, lead, platinum or different metal alloys. The bioceramic material is preferably a material that may crack under deformation but retains its shape. In the case of polymers and composites, the material should retain the shape into which it has been bended. Suitable polymers for the sheet are polyvinylchloride, polyethylene, polycarbonate, polyamide and polyesters.

According to an embodiment of the invention, the inner surface of the casing is treated so as to provide an active surface to the finished implant. This can be achieved in several ways, for example by roughening the surface or by coating it with active material.

According to an embodiment of the invention, the inner surface of the casing is porous so as to provide a rough surface to the finished implant. Indeed, a nanosurface topography of the finished implant impressed by the surface texture of the casing during the manufacture of the implant increases mineralization of the hydroxy apatite minerals of bone on the implant surface by offering nucleation sites for hydroxy apatite crystals (Ref: Webster T J, Ergun C, Doremus R H, Siegel R W, Bizios R: Specific proteins mediate enhanced osteoblast adhesion on nanophase ceramics. J Biomed Mater Res 2000; 51:475-483).

According to another embodiment of the invention, the inner surface of the casing is treated with a coating selected from the group consisting of coating obtained by sol-gel process, bioactive glass particles, fibronection, vitronection, hydroxyapatite, therapeutically active agents or particles releasing therapeutically active agents, cells and mixtures thereof, so as to provide a chemically active surface to the finished implant. The casing may thus be coated, for example, with a layer of biologically active substances, such as particulates of bioactive glass, hydroxyapatite, other bioceramics, polysaccharide, adhesive, fibronection, vitronection, fibrogen, Arg-Gly-Asp peptide, laminin, drug releasing particles, sol-gel processed bioceramics, proteins, growth factors, antibiotics or cells. Any combination of these materials may also be used. See for example Miller D C, Haberstroh K M, Webster T J: PLGA nanometer surface features manipulate fibronection interactions for improven vascular cell adhesion. J Biomed Mater Res 2007; 81 A:678-684.

It is naturally possible that the casing's inner surface is both porous and comprises a coating, such as described above. There can thus be a nano- to millimeter scale surface topography on the inner surface of the casing, which will then be impressed and copied to the surface of the finished implant for improving the attachment of hard or soft tissues to the implant surface during the healing period of the patient.

According to yet another embodiment of the invention, at least 10% of the surface of the casing comprises the sheet-like material. According to another embodiment, at least 30% of the surface of the casing comprises the sheet-like material. According to another embodiment, at least 50% of the surface of the casing comprises the sheet-like material. According to yet another embodiment, at least 900% of the surface of the casing comprises the sheet-like material Indeed, the casing can be fully made of a sheet-like material selected from metallic materials or bioceramic materials, or it can be only partly made of such materials. It may also be made of a multilayer material, wherein at least one of the layers comprises such sheet-like material. The amount of the surface comprising this kind of material can be, for example, from 5, 10, 15, 20, 25, 30, 35, 40, 45, 50, 60, 65, 70, 85, 90 or 95% up to 10, 15, 20, 25, 30, 35, 40, 45, 50, 60, 65, 70, 85, 90, 95, 99 or 100% of the total surface.

The casing and the bag, i.e. the inner and outer enclosures of the implant material may be manufactured from any suitable material. According to a preferred embodiment of the invention, the casing (i.e. the inner enclosure) is manufactured from a material that can be modeled, that is, its shape can be easily modified, but that then maintains the shape, thus maintaining the implant material in the form of the anatomical requirements of the final implant. As an example, the casing may be manufactured from metal foil or web, or it may be a composite of metal and another material. Preferably, the casing is made of a material consisting essentially of metal. It is also possible that the casing is made of a material which is permanently deformed during the shaping of the implant material.

On the other hand, the bag (i.e. the outer enclosure) can be made of a material selected from the group consisting of metals and polymers. The most important function of the bag is to protect the implant material and casing from outside aggressions, such as oxygen and light, and to keep the implant material and casing sterile before use.

The metal used may be selected from the group consisting of aluminium, tin, platinum and metal alloys. If tin is used, it needs typically to be insulated from the monomers for example by a plastic enclosure. The polymer may be selected from the group consisting of polyethylene, polyethylene terephthalate, polyamide, polyurethane, polyester, polyvinylsiloxane, polyetherketone, polyacrylate, polyglycolide, polylactide and mixtures thereof.

There may also be several different enclosures in addition to the inner casing and the outer bag. The casing and the bag themselves may also contain several layers of materials. For example, the bag may be non-transparent to light while the casing may be partially or completely transparent to light, or only transparent to the curing light.

According to an embodiment of the invention, the casing consists of two parts, an inner transparent vacuum part and an outer non-transparent protecting part. The inner part consists thus of a vacuum package and contains the implantable material. This vacuum package can be made, for example, for plastics, such as polyethylene. The vacuum package is contained in a outer part of the casing consisting of an non-transparent protecting part, i.e an environmental light protecting part. This outer part can then have an opening designed to receive the light emission tip of a light curing device, such as photopolymerisation device. The environmental light protecting package can be made, for example, from metal.

According to an embodiment of the invention, the inner surface of the casing is light-reflecting, thus allowing the manufacture of a fully cured implant while the implantable material is still inside a closed and sterile casing. The light-reflecting surface may be made, for example, from metal, such as silver, aluminium or tin. The curing light may be, for example, in the wave length area of 440-500 nm.

The implant material used in the present invention may be any suitable material, but would naturally need to be biocompatible. Preferably, the implant material is selected from the group consisting of bioactive glass, bioactive polymer and mixtures thereof. The implant material may comprise both a matrix and filler material, and the filler can be in the form of fibres or particles. When the finished implant is a composite material, the implantable material may also be called a prepreg.

The implantable material may further contain precured parts for specific functions in the finished implant, such as cylinders for fixation of the implant with screws. The cylinders may be, for example, precured cylinders which can be positioned according to the anatomical requirements of the final implant, inside the inner package (the casing) before curing of the implant.

The present invention further relates to an implant obtainable by curing an implant system according to the present invention. All the embodiments and details described above in relation to the implant system apply mutatis mutandis to the implant. The implant according to the present invention may be, for example, a bone implant, a dental implant, an implant for hearing aid device or cosmetic epithese implant.

Some examples of uses of the present implant system and implant are long bone repair applications, such as bone fixation plates, nails, joint prostheses, joint resurfacing material; repairs of calvarial bones; repair of bones of maxillofacial region; dental implants to be inserted to an extraction socket or used in holes drilled to the jaw bones; in hearing bones of ears and implants for hearing aid devives; for fabrication of cosmetic epithese implants; in dentistry to make the shaping and positioning of fibre-reinforce composite prepregs easier to adapt to the tooth surfaces.

According to an embodiment of the invention, the implant system is such that it can be cured, for example, in 60 seconds or less with light. If ultraviolet light is used, either for curing or in addition to curing, sterilisation of the implant is obtained at the same time.

The present invention further relates to a method for manufacturing an implant using the present implant system. The method comprises the steps of
  removing the closed bag containing the casing,
  positioning the casing containing the implantable material to the final position of the finished implant,
  curing the implant material,
  removing the casing containing the cured implantable material from the final position of the finished implant, and
  removing the casing to obtain the finished implant.

Thereafter, the surgeon positions the finished implant to its final position, such as the surgical site or tooth. The advantage of this method is that it allows the use of non-sterilised raw materials and thus lowers the cost of the implant material and makes it less sensible for storage problems.

Alternatively, the casing may be removed from the final position before curing the implantable material, or the implantable material may be pre-cured by light in vivo and the curing be finished ex vivo.

Ex vivo post-polymerization of the composite prepreg by increased temperature or microwaves after initial polymerisation of the material by light increases the degree of monomer conversion of the polymer matrix, which in turn improves the biocompatibility of the material due to a decreased quantity of residual monomers (Ref: Viljanen E K, Skrifvars M, Vallittu P K. Degree of conversion of an experimental monomer and methyl methacrylate copolymer for dental applications. J Appl Polym Sci 2004; 93:1908-1912; Vallittu P K, Ruyter I E, Buykuilmaz S. Polymerization time and temperature affects the residual monomer content of denture base polymers. Eur J Oral Sci 1998; 106:588-593).

DESCRIPTION OF THE DRAWINGS

FIG. 1 shows a cross-sectional view of an implant system according to a first embodiment of the invention. The implant system 1 consists of implantable material (prepreg) consisting of fibres 2 and matrix material 3. The fibres 2 are in the form of a woven mesh. The prepreg is contained in a casing consisting of a vacuum package 4 made of polypropylene with an inner surface coated with light reflecting material. Furthermore, the vacuum package has on one side a sheet 5 made of metal that can be easily bent to the required shape and yet maintains the shape.

Figure 2:
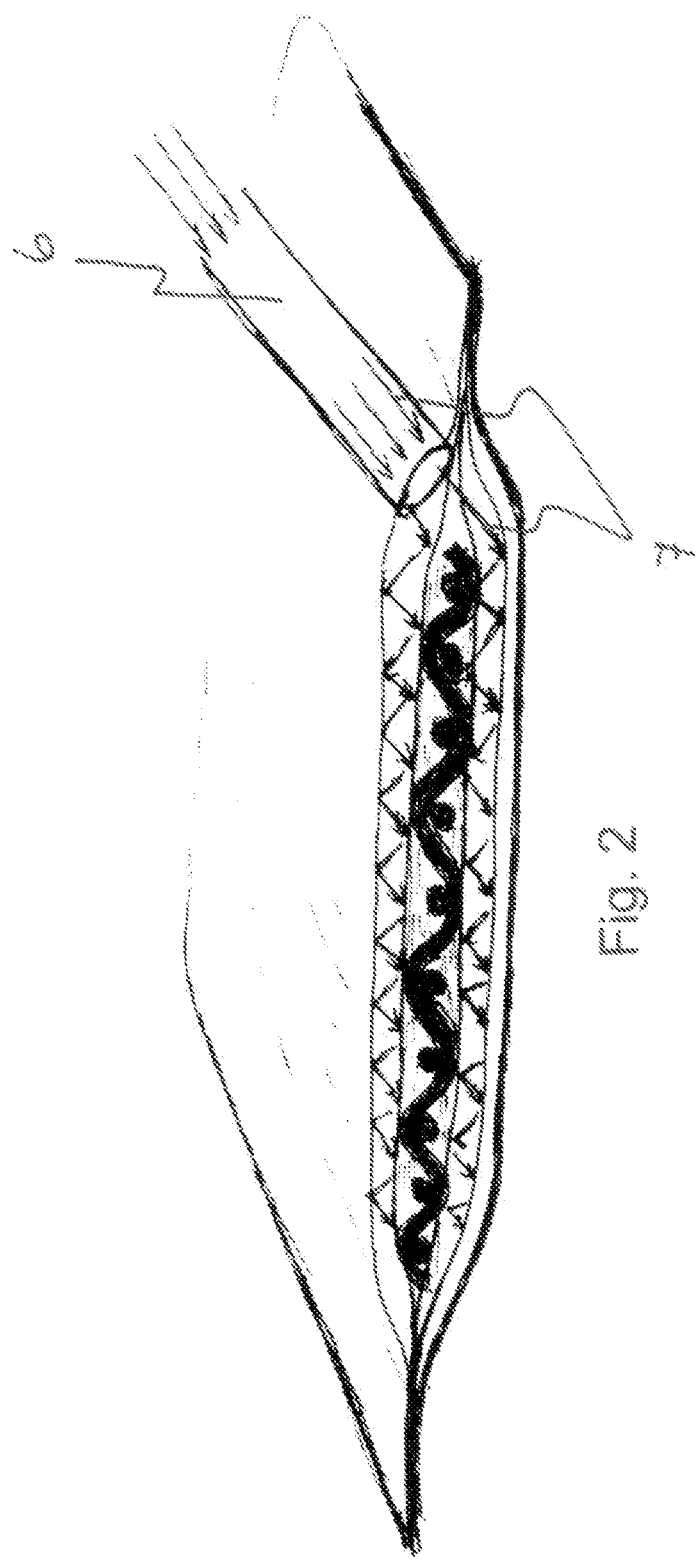
FIG. 2 shows the implant system of FIG. 1 during curing.

FIG. 2 shows the implant system of FIG. 1 during curing. A tip 6 of a light curing device (not shown) is introduced to an opening of the casing. The light 7 enters the casing in order to cure the prepreg, and reflects from the inner surface of the casing so that the whole implant system is cured.

Figure 3:
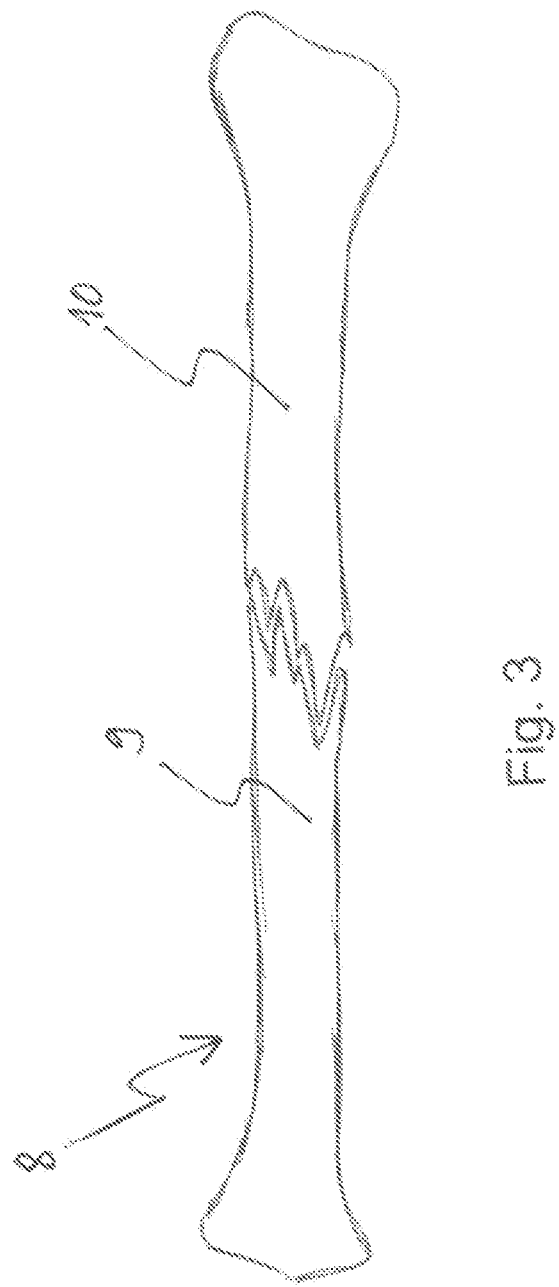
FIG. 3 shows a use of an implant system according to the invention.

FIG. 3 shows a use of an implant system according to the invention. A bone 8 has been fractured to two parts, 9 and 10. The implant system according to the invention is placed around the fracture area and cured to shape. The casing is then removed and the implant secured to place by screws or glue.

FIG. 4 shows a use of an implant system according to a second embodiment of the invention. In this embodiment, the implant system 11 consists of unidirectional fibres 12 embedded in a matrix 13. The implant system is first positioned in a socket 14 left by a tooth and cured either in situ or outside the patient's mouth. Once the casing is removed, the implant is ready to be replaced into the socket 14 in order to form a basis for a tooth implant.

EXPERIMENTAL PART

Example 1

An implant system for long bone fixation plate to be polymerised in situ was made as follows: non-cured implant prepreg material (i.e. implantable material) in the average form and size of a long bone fracture fixation plate (18 mm in length, 14 mm in width and 3 mm in thickness) was placed to a vacuum package of polyethylene sheets thus forming an inner part of the casing. The vacuum package with the implant prepreg therein was placed to an environmental light protecting package (i.e. an outer part of the casing) having an opening in one end of the package for the light emission tip of a photopolymerization device. The environmental light protecting package was made of aluminium having a thickness of 0.05 mm.

These two packages were then placed into a covering package after which the implant prepreg and the packages were sterilized. During the surgical procedure, the covering package of the implant was removed and the implant with the environmental light protecting package was manually pressed against the bone repair area in order to shape the implant to the shape of the existing pieces of bones, for obtaining a good fit. The aluminium foil of the environmental light protecting package remains in this shape due to its permanent deformation.

A light tip made of optical fibres was placed to the opening of the package and light with wave length of 460-470 nm was emitted from the light tip during 40 seconds. As the light reflected from the inner surface of the aluminium environmental light protecting package, the prepreg was polymerised to the shape of the aluminium package.

The implant was removed from the environmental light protecting package and from the vacuum package and screwed or glued on place to support the bone fragments.

Example 2

An implant system for long bone fixation plate to be formed in situ and polymerised with a light curing device at the operation theatre was made as follows: the non-cured implant prepreg material of a polymeric-based composite of bis-GMA resin system and S-glass (high strength glass) fibers containing a titanium mesh of 0.1 mm in thickness for providing adequate radio-opacity and supporting the metal foil to retain the shape is used in the average form and size of long bone fracture fixation plate (18 mm in length, 14 mm in width and 3 mm in thickness) was placed to the vacuum package of polyethylene sheets. The vacuum package had, as an integral part, a metal foil as one surface of the package enabling bending and forming of the prepreg to correspond to the bone. The package remains the form by permanent deformation of the metal foil and the prepreg can be placed in its anatomical form to the light curing device and be polymerised. The casing is thus formed from a combination of plastic and metal.

After polymerisation by light, the package was opened and the implant was removed, placed to the operation area and fixed by screws or bioadhesives to the bone.

Example 3

An implant system was prepared, with polymerised particulate filler or metal fixation cylinders within the prepreg. The fixation cylinders were attached by mechanical retentions to the fibre structure of the composite implant prepreg. Before polymerisation of the prepreg, the fixation cylinders could be moved and angulated inside the package by sliding the cylinders in the prepreg material. During polymerisation, the fixation cylinders were attached to the prepreg and were used in fixation of the implant by screws.

Example 4

An implant system was used in fabrication of a custom-made calvarial and maxillofacial implant on a rapid prototyping model based on a computer tomography images of the patient. The damaged bone area of the skull was covered with the implant system and shaped to the required anatomical form. The form was hold by the permanent deformation of the metal foil of the implant system and the prepreg was polymerised in a light curing device. After polymerisation, the implant was removed from the package, formed to the final shape by adjusting the margins of the implant and placed to the post-curing device for reaching a final degree of curing. Finally, the finished implant was placed to a delivering package and sterilized.

Example 5

An implant system comprising continuous unidirectional fibres and having the average shape of root of a tooth was prepared. The outermost surface of the casing was made of a metal foil enabling bending, thus causing permanent deformation to the metal foil once the casing of the implant system was inserted to an extraction socket. After removal from the socket, the metal foil remained in the shape of the socket and the prepreg was polymerized from an open end of the package by blue light. The inner aluminium surface reflecting the light inside the package increased the degree of monomer conversion of the resin system of the prepreg.

Example 6

Use of an implant system according to this invention in splinting of teeth and in fabrication of dental bridges was tested. A metal foil on one side of the casing retained the shape of the tooth surface by permanent deformation of the metal once it was pressed against the tooth surface. The shape of the metal foil also retained the fibres of the prepreg in the casing in the area of the metal foil, thus eliminating any spreading of the fibres to an incorrect location. The prepreg was either removed from the mouth and light polymerised inside the package with one transparent surface, or polymerised directly against the tooth surface with the help of a metal foil, followed by removal of the foil.

The invention claimed is:

1. An implant system comprising
   implantable material in at least partially uncured form, contained in a closed casing, under vacuum and sterilised,
   a closed bag containing the casing,
   wherein at least 5% of the surface of the casing comprises sheetlike material having a thickness of 0.05-5 mm and having an original form, the sheet-like material being selected from the group consisting of metallic materials, polymers, bioceramic materials and composites thereof, provided that the material, once deformed from its original form to a changed form, is capable of maintaining that changed form unless subjected to external force, and
   wherein an inner surface of the casing is treated such that said inner surface can provide an active surface to an implant manufactured from said implantable material.

2. An implant system according to claim 1, wherein the inner surface of the casing is porous so as to provide a rough surface to said implant.

3. An implant system according to claim 1, wherein the inner surface of the casing is treated with a coating selected from the group consisting of coating obtained by sol-gel process, bioactive glass particles, fibronectin, vitronection, fibrogen, polysaccharide, Arg-Gly-Asp peptide and laminin, hydroxyapatite, therapeutically active agents or particles releasing therapeutically active agents, cells and mixtures thereof, so as to provide a chemically active surface to said implant.

4. An implant system according to claim 1, characterised in that at least 50% of the surface of the casing comprises the sheet-like material.

5. An implant system according to claim 4, characterised in that at least 90% of the surface of the casing comprises the sheet-like material.

6. An implant system according to claim 1, characterised in that the thickness of the sheet-like material is 0.1-0.5 mm.

7. An implant system according to claim 1 characterised in that the sheet-like material is selected from the group consisting of plate, foil, flat wire, mesh and a combination of any two, three or four thereof.

8. An implant system according to claim 1, characterised in that the casing is made of a material consisting essentially of metal.

9. An implant system according to claim 8, characterised in that the metal is selected from the group consisting of aluminium, tin, platinum and metal alloys.

10. An implant system according to claim 1, characterised in that the bag is made of a material selected from the group consisting of metals and polymers.

11. An implant system according to claim 10, characterised in that the polymer is selected from the group consisting of polyethylene, polyethylene terephtalate, polyamide, polyurethane, polyester, polyvinylsiloxane, polyetherketone, polyacrylate, polyglycolide, polylactide and mixtures thereof.

12. An implant system according to claim 1, characterised in that the casing consists of two parts, an inner transparent vacuum part and an outer non-transparent protecting part.

13. An implant system according to claim 1, characterised in that the inner surface of the casing is light-reflecting.

14. An implant system according to claim 1, characterised in that the implant material is selected from the group consisting of bioactive glass, bioactive polymer and mixtures thereof.

15. An implant system according to claim 1, wherein the implantable material further comprises precured parts suitable for specific functions in said implant.

16. An implant system according to claim 15, characterised in that the precured parts are cylinders for fixation of the implant with screws.

17. An implant obtainable by curing an implant system according to claim 1.

18. An implant according to claim 17, characterised in that it is a bone implant, a dental implant, an implant for hearing aid device or cosmetic epithese implant.

* * * * *